United States Patent [19]

Bartner

[11] 4,305,947

[45] Dec. 15, 1981

[54] STABLE AQUEOUS SOLUTIONS OF PRALIDOXIME SALTS

[75] Inventor: Elliot Bartner, Piscataway, N.J.

[73] Assignee: Survival Technology, Inc., Del.

[21] Appl. No.: 182,305

[22] Filed: Aug. 26, 1980

[51] Int. Cl.$^3$ ............... A61K 31/44; C07D 271/00; C07D 487/00; C07D 491/00; C07D 495/00; C07D 497/00; C07D 498/00; C07D 513/00
[52] U.S. Cl. ............................ 424/263; 546/338
[58] Field of Search ................. 424/263; 546/338

[56] References Cited

U.S. PATENT DOCUMENTS 2,816,113 12/1957 Wilson et al. ................ 424/263
2,996,510 8/1961 Green ..................... 424/263 X
3,629,425 12/1971 Hussain ....................... 424/263

OTHER PUBLICATIONS

Chem. Abstr. 61:14474g (1964).
Merck Index 9th Ed. No. 4731 (1976).

*Primary Examiner*—Frank Cacciapaglia, Jr.
*Attorney, Agent, or Firm*—Cushman, Darby & Cushman

[57] ABSTRACT

Aqueous solutions of pralidoxime salts are stabilized with hydroxylamine salts.

10 Claims, No Drawings

STABLE AQUEOUS SOLUTIONS OF PRALIDOXIME SALTS

BACKGROUND OF THE INVENTION

As disclosed in Wilson U.S. Pat. No. 2,816,113 2-[(hydroxyimino)methyl]-1-methylpyridinium chloride (Pralidoxime chloride, 2-PAM chloride) is useful as an inhibitor of cholinesterase and is particularly useful as a specific antidote against lethal alkyl phosphate intoxication.

Aqueous 2-PAM chloride solutions have a tendency to be unstable, particularly at elevated temperature. Hussain U.S. Pat. No. 3,629,425 proposes the stabilization of 2-PAM salts (e.g. 2-PAM chloride) by adding an inorganic acid in an amount sufficient to reduce the pH of the 2-PAM chloride to a pH within the range of 1.0 to 3.0 and then storing the thus stabilized 2-PAM chloride.

SUMMARY OF THE INVENTION

It has now been found that aqueous solutions of 2-PAM salts and particularly 2-PAM chloride can be stabilized by adding an effective amount of hydroxylamine hydrochloride. The pH of the solution is between 3.0 and 4.0. However, upon autoclaving at 121° C. for 20 minutes the pH falls to below 3.0.

The concentration of the 2-PAM chloride (or other salt, e.g. hydrogen sulfate, nitrate, fumarate, lactate, tartrate or methane sulfonate) in the aqueous solution is not critical and can be, for example, from 10 percent on a weight per volume basis (w/v) up to the solubility limit of the 2-PAM salt. The concentration of hydroxylamine hydrochloride also is not critical so long as it is sufficient to impart stability. The hydroxylamine chloride can be used up to its solubility limit.

The composition can comprise, consist essentially of or consist of the stated materials.

Unless otherwise indicated all concentrations are on a weight per volume basis.

2-PAM chloride in aqueous solution, e.g. 300 mg/ml was autoclaved for 20 minutes at 15 lbs pressure (121° C.). There was immediate color formation, the color increasing with each autoclaving treatment. It was also noted that the pH of the solution fell from approximately 4.0 to 2.5 with continued autoclaving.

DETAILED DESCRIPTION OF THE INVENTION

EXAMPLE 1

There was prepared a solution of the following composition:

3.0 grams Pralidoxime chloride (2-PAM chloride)
150 mg hydroxylamine hydrochloride
q.s. 10 ml of distilled water.

Thus there were 300 mg/ml of Pralidoxime chloride and 15 mg/ml of hydroxylamine hydrochloride.

The pH of the solution was between 3.0 and 4.0. After being subjected to 4 separate 20 minute autoclaving treatments of 121° C., the solution remained essentially colorless and the pH was in the range of 1.8–1.9. Similar solutions without hydroxylamine hydrochloride subjected to this treatment were highly colored (yellow-orange-red) and did not drop in pH to the same range.

EXAMPLE 2

In this example there were tested as stabilizers different concentrations of hydroxylamine hydrochloride in aqueous solution. Two runs were made at each concentration and two blanks were run. The stability tests were carried out by autoclaving for 20 minute intervals at 121° C. for 5 times followed by two autoclavings for 50 minutes each at 121° C. Thus there was a total autoclaving time of 200 minutes. The pH was measured after the autoclaving. The concentration of the Pralidoxime chloride was 300 mg/ml and the samples contained 3.0 grams of the Pralidoxime in 10 ml of water.

The products were analyzed after the autoclaving treatment.

TABLE 1

| Run | Hydroxylamine Hydrochloride (mg/ml) | Concentration of Pralidoxime Chloride after autoclaving (mg/ml) | pH after final autoclaving |
|---|---|---|---|
| 1A | 5 | 278 | 1.6 |
| 1B | 5 | 284 | 1.6 |
| 2A | 10 | 299 | 1.5 |
| 2B | 10 | 278 | 1.5 |
| 3A | 15 | 293 | 1.4 |
| 3B | 15 | 281 | 1.4 |
| 4A | 0 | 188 | 2.6 |
| 4B | 0 | 210 | 2.6 |

EXAMPLE 3

In order to show the criticality of using the hydroxylamine salt rather than simply an acid there were made up solutions as in Example 2 but utilizing in one case hydroxylamine hydrochloride in an amount of 10 mg/ml to give an initial pH of 3.19 and in the other case hydrochloric acid in amount to give an initial pH of 3.09. Blank runs were also made. Autoclaving was carried out in the manner set forth in Example 2.

TABLE 2

| Run | Hydroxylamine Hydrochloride mg/ml | HCl to pH 3.09 | Concentrations of Pralidoxime Chloride after autoclaving (mg/ml) | pH after final autoclaving |
|---|---|---|---|---|
| 5A | 10 | No | 249 | 1.4 |
| 5B | 10 | No | 241 | 1.5 |
| 6A | 0 | Yes | 126 | 2.6 |
| 6B | 0 | Yes | 141 | 2.8 |
| 7A | 0 | No | 143 | 2.6 |
| 7B | 0 | No | 122 | 2.6 |

In place of hydroxylamine hydrochloride there can be employed other salts of hydroxylamine such as hydroxylamine hydrobromide, hydroxylamine sulfate, hydroxylamine phosphate, hydroxylamine nitrate.

There can also be present with the Pralidoxime chloride (or other 2-PAM salt) other materials such as atropine or atropine salts, e.g. atropine sulfate, commonly used in the therapeutic dosages with 2-PAM salts.

The stabilized 2-PAM salt solutions of the present invention can be made up in conventional form, e.g. in injectable ampules or vials or cartridges.

It has been found that hydroxylamine hydrochloride is effective as a stabilizer for 2-PAM chloride at a concentration of 1 mg/ml and is increasingly effective up to 10 mg/ml.

What is claimed is:

1. A stable aqueous solution comprising at least 100 mg/ml of a pralidoxime salt which is the chloride, hydrogen sulfate, nitrate, fumarate, lactate, tartrate, or methane sulfonate and at least 5 mg/ml of a hydroxylamine salt which is hydrochloride, hydrobromide, sulfate, phosphate, or nitrate.

2. A stable solution according to claim 1 wherein the hydroxylamine salt is the hydrochloride.

3. A stable solution according to claim 2 wherein the pralidoxime salt is the chloride.

4. A stable solution according to claim 3 wherein the concentration of the hydroxylamine hydrochloride is 5 to 15 mg/ml.

5. A composition according to claim 4 consisting of water, hydroxylamine hydrochloride, and pralidoxime chloride.

6. A stable aqueous solution according to claim 4 wherein the pH is not over 4.0.

7. A stable aqueous solution according to claim 1 wherein the pH is not over 4.0.

8. A stable aqueous solution according to claim 1 wherein the pH is 1.4 to 4.0.

9. A stable aqueous solution according to claim 1 wherein the pH is 3.0 to 4.0.

10. A stable aqueous solution according to claim 1 wherein the pralidoxime salt is the methanesulfonate.

* * * * *